United States Patent
Nadeau et al.

(10) Patent No.: US 7,981,411 B2
(45) Date of Patent: Jul. 19, 2011

(54) USE OF LIVE BACTERIA FOR GROWTH PROMOTION IN ANIMALS

(75) Inventors: Eric Nadeau, Otterburn Park (CA); John Morris Fairbrother, St-Hyacinthe (CA)

(73) Assignee: Valorisation—Recherche, Limited Partnership, Montreal, QC ( * ) Notice: Subject to any disclaimer, the term of this patent is extended or adjusted under 35 U.S.C. 154(b) by 681 days.

(21) Appl. No.: 10/587,960

(22) PCT Filed: Feb. 3, 2005

(86) PCT No.: PCT/CA2005/000138
§ 371 (c)(1),
(2), (4) Date: Mar. 22, 2007

(87) PCT Pub. No.: WO2005/074706
PCT Pub. Date: Aug. 18, 2005

(65) Prior Publication Data
US 2007/0218035 A1    Sep. 20, 2007

(51) Int. Cl.
*C12N 1/20* (2006.01)
*C12P 1/04* (2006.01)
(52) U.S. Cl. ..... 424/93.4; 435/170; 435/243; 435/252.8
(58) Field of Classification Search .................. 424/93.4; 435/170, 243, 252.8
See application file for complete search history.

(56) References Cited

U.S. PATENT DOCUMENTS

| | | | |
|---|---|---|---|
| 4,761,372 A | | 8/1988 | Maas et al. |
| 5,137,721 A | * | 8/1992 | Dallas ........................ 424/200.1 |
| 6,500,423 B2 | | 12/2002 | Olshenitsky et al. |
| 6,511,661 B2 | * | 1/2003 | Olshenitsky et al. ........ 424/93.3 |

FOREIGN PATENT DOCUMENTS

| | | |
|---|---|---|
| EP | 0060129 A2 | 9/1982 |
| WO | WO-99/08532 | 2/1999 |
| WO | WO2007/136553 A2 | 11/2007 |

OTHER PUBLICATIONS

Arnold S., Gassner B., Giger T. end Zwahlen R. Banning antimicrobial growth promoters in feedstuffs does not result in increased therapeutic use of antibiotics in medicated feed in pig farming, Pharmacoepidemiology and Drug Safety 2004; 13; 323-331.

Wegener HC, Asrestrup FM, Bogo Jensen L, Hammerum AM and Bager F, Use of antimicrobial growth promoters in food animals and *Enterococcus faecium* resistance to therapeutic antimicrobial drugs in Europe. Emerging Infectious Diseases 1999; 5(3): 329-335.

Schwarz S, Ketrenberg C and Walsh TR, Use of antimicrobial agents in veterinary medicine and food animal production. International Journal of Antimicrobial Agents 2001; 17: 431-437.

Bernardeau M, Vemoux JP and Gueguen M. Safety and efficacy of probiotic lactobacilli in promoting growth in post-weaning Swiss mice. International Journal of Food Microbiology 2002; 77(1-2): 19-27.

Alexa et al. (1995). "Combined Parenteral and Oral Immunization Against Diarrhea in Weaned Piglets Caused by Enterotoxigenic Strains of *Escherichia coli*," Vet. Med.—Czech. 40(12):365-370. (English Abstract).

Bianchi et al. (1996). "Parenteral vaccination of mice and piglets with F4+ *Escherichia coli* suppresses the enteric anti-F4 response upon oral infection," Vaccine. 14(3):199-206.

Melin and Wallgren. (2002). "Aspects on Feed Related Prophylactic Measures Aiming to Prevent Post Weaning Diarrhoea in Pigs," Acta Vet. Scand. 43(4):231-245.

Snoeck et al. (2003). "Enteric-coated pellets of F4 fimbriae for oral vaccination of suckling piglets against enterotoxigenic *Escherichia coli* infections," Veterinary Immunology and Immunopathology. 96:219-227.

Supplementary Europen Search Report for EP05706458, dated Oct. 13, 2009.

Chesnokova, et . (1999) "*Escherichia coli* Strain M17: Analysis of Adhesive Phenotype as a Factor of Host Colonization and/or Pathogenicity," Bulletin of Exp. Biology and Medicine, vol. 4, pp. 386-389.

Evans et al. (1990) "Colonization Factor Antigens of Human Pathogens," Current Topics in Microbiology and Immunology, vol. 151, pp. 129-145.

Moon (1990) "Colonization Factor Antigens of Enterotoxigenic *Escherichia coli* in Animals," Current Topics in Microbiology and Immunology, vol. 151, pp. 147-165.

* cited by examiner

*Primary Examiner* — Ruth A Davis
(74) *Attorney, Agent, or Firm* — Choate Hall & Stewart LLP; Charles E. Lyon

(57) ABSTRACT

The present invention relates to the use of F4+ non-pathogenic *Escherichia coli* strains to promote growth in an animal. The present invention also relates to the use of such strains to homogenize growth among a herd of animals. More specifically, the animal(s) of interest in the present invention are those wherein growth promotion or growth homogenization are desired goals, such as animals reared for meat production. The present invention further relates to a method for promoting growth of an animal as well as a method for homogenizing growth among a herd of animals.

19 Claims, 3 Drawing Sheets

USE OF LIVE BACTERIA FOR GROWTH PROMOTION IN ANIMALS

FIELD OF THE INVENTION

The present invention relates to the field of growth promotion in animals. More specifically, the present invention relates to the use of a non-pathogenic *Escherichia coli* strain expressing the F4 (or K88) attachment factor, to either promote growth in animals or homogenize growth among a herd of animals.

BACKGROUND OF THE INVENTION

Growth promotion is a crucial issue for farm and breeding specialists, who mainly seek to optimize the production of healthy animals before slaughter or for research purposes. Such a concern should lead them to use growth promoting products that would prove beneficial to the animals and also to humans, in the case of meat-producing animals.

One major caveat in farms and breeding environments is the weight loss, slow growth rate along with a recrudescence of concomitant diseases, drug cost, and mortality which lead to a decrease in animal yields and ultimately to considerable economic losses. In this connection, post-weaning or post-hatching animals are particularly vulnerable to agents impeding growth.

Infections caused by either non-hygienic conditions or close proximity between animals, for example, are among the most common factors leading to the above-mentioned caveat.

One conventional solution used to alleviate this problem has been to use antibiotic growth promoters in feeds. However, use of antibiotic growth promoters is also highly controversial because, as is well known, even at sub-therapeutic doses, continued antibiotic use can lead to selection of antibiotic-resistant bacterial strains in the treated animals (Arnold S et al.; Wegener HC et al. and Schwarz S et al.). In fact, in the last ten years, there has been an emergence of more pathogenic and more antibiotic-resistant *Escherichia coli* strains and/or husbandry changes (early weaning) and/or new European regulations forbidding use of antimicrobial agents as growth promoters or for prophylaxis treatment (prevention of diseases) and use of high levels of heavy metals, such as zinc oxide in the feed. The weaning period is particularly associated with higher antibiotic use during animal production.

Consequently, there is now a growing resistance to the use of antibiotic growth promoters and heavy metals due to recrudescence of antibiotic resistance, allergic reactions to antibiotic residues, and contamination of cultivated soil.

Another caveat that farm and breeding specialists also have to face is growth heterogeneity among herds of animals. More specifically, in a purpose of optimized meat production for example, farmers seek to produce consistent herds of animals displaying the most homogeneous growth rate possible before slaughter, to avoid increased costs. However, animals generally present different rates of growth and different vulnerabilities to infectious agents, among others.

There is thus a constant need for innovating agents that promote growth of animals and that advantageously further contribute to homogenize and optimize animal growth.

SUMMARY OF THE INVENTION

An object of the present invention is to use of an effective amount of an F4+ non-pathogenic *Escherichia coli* strain to promote growth in an animal.

Another object of the present invention is to use of an effective amount of an F4+ non-pathogenic *Escherichia coli* strain to homogenize growth among a herd of animals.

A further object of the present invention is to provide a method of promoting growth in an animal, said method comprising the step of feeding said animal with an effective amount of an F4+ non-pathogenic *Escherichia coli* strain.

Yet another object of the present invention is to provide a method of homogenizing growth among a herd of animals, said method comprising the step of feeding said animals with an effective amount of an F4+ non-pathogenic *Escherichia coli* strain.

Owing to the use of F4+ non-pathogenic *Escherichia coli* strains, the invention finds an advantage in situations wherein rapid growth promotion and growth homogenization of an animal are particularly needed. For instance, use of $F4^+$ non-pathogenic *Escherichia coli* strains in animals reared for meat production allows to bring these animals to market weight or slaughter weight in a shorter growing period than that of their untreated counterparts.

The present invention may further find an advantage for growth promotion and growth homogenization of laboratory animals, such as rats and mice. As can be appreciated, bringing these laboratory animals to a given weight faster and more homogeneously preferably provides for more homogeneous and readily available samples of animals.

Another advantage of the present invention is that there is no recourse to antibiotic use to promote growth in animals. Therefore, problems such as development of antibiotic-resistant bacterial strains or allergies to antibiotics which particularly affect post-weaning animals, are alleviated.

Moreover, since heavy metals such as zinc oxide are not added to the animal's feed, contamination of the soil is also avoided. In other words, the present invention also provides for environment-friendly uses and methods.

The improved efficiency of feed conversion attained by the present method enables treated animals to reach any desired weight while consuming less food than untreated animals grown to the same weight. Moreover, while practicing the method of the present invention, neither toxic side effects nor decrease in general health status due to the bacterium is observed in the treated animals.

The invention and its advantages will be better understood upon reading the following non-restrictive description of preferred embodiments thereof, made with reference to the accompanying drawings.

DETAILED DESCRIPTION OF THE INVENTION

Figure 1:
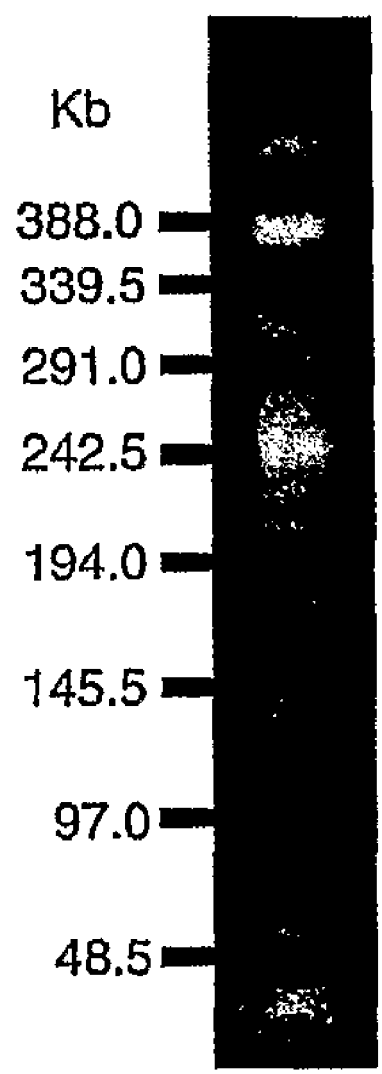
FIG. 1 is a photograph showing the pulsed-field gel electrophoresis pattern of Xbal-digested genomic DNA of a preferred $F4^+$ non-pathogenic *Escherichia coli* strain used in accordance with the present invention. The preferred strain is the coliPROtec strain.

The originality of the present invention stems from new uses for $F4^+$ non-pathogenic *Escherichia coli* strains. More particularly and according to a first aspect, the present invention relates to the use of an effective amount of an $F4^+$ non-pathogenic *Escherichia coli* strain to promote growth in an animal.

According to a second aspect, the present invention relates to the use of an effective amount of an $F4^+$ non-pathogenic *Escherichia coli* strain to homogenize growth among a herd of animals.

According to related aspects, the present invention relates to a method of promoting growth in an animal and to a method of homogenizing growth among a herd of animals.

Both methods comprise the step of feeding the animal(s) with an effective amount of an F4+ non-pathogenic *Escherichia coli* strain.

The strain used in the present invention is characterized in that it expresses the attachment factor F4, while being non-pathogenic. According to a preferred aspect of the invention, the F4+ non-pathogenic *Escherichia coli* strain is selected from the group consisting of coliPROtec (Accession number IDAC 210105-01), JG1329, M226, P03-7586(175) or pMK005. More preferably, the present invention contemplates using the coliPROtec strain and/or mutants or variants thereof (see Example I for more details).

As used herein, the terms "mutants" and "variants of the coliPROtec strain are used for strains that have all the identifying characteristics of the coliPROtec strain, as provided in Example I. Mutant or variant strains may be identified as having a genome or part thereof that hybridizes under conditions of high stringency to the genome of the coliPROtec strain.

According to the above-mentioned aspects of the invention, the above-described strain is used in an "effective amount". By the expression "effective amount", it will be understood that the amount of an F4+ non-pathogenic *Escherichia coli* strain is the amount that will elicit the biological response of a tissue, system or animal that is being sought by the researcher or the veterinarian, for example. In other words, such an effective amount of an F4+ non-pathogenic *Escherichia coli* strain is the amount that is sufficient for promoting growth in an animal as well as homogenizing growth among a herd of animals.

It will be understood that a preferred effective amount of the strain contemplated by the present invention is at least about $5^{E}7$ colony-forming units (CFU), and more preferably range from about $5^{E}7$ to about $5^{E}9$ CFU of the strain of interest per animal. By "about", it is meant that the CFU value of said strain can vary within a certain range depending on the margin of error of the method used to evaluate the number of CFU for such a strain.

The effective amount to be used may vary according to a number of factors. For instance, type of animal, initial weight of the animal, growth phase of the animal, environment i.e. animal facilities, type and management of production, hygienic status of the facilities, stress after weaning or hatching, feed and supplements used, health of the animal and concomitant diseases or treatment, may be factors to take into account.

As mentioned above, the objectives of growth promotion and growth homogenization are achieved in an animal. As used herein, the term "animal" refers to any young or adult animal suitable to be used in accordance with the present invention. More preferably, the term "animal" refers to a post-weaning or a post-hatching animal.

Since in either a post-weaning or post-hatching animal, maternal feeding and caring are no longer available, growth promoting agents are of the utmost importance. Such a concern is particularly crucial, for instance, in the case of animals bred for their meat.

In the context of the present invention, preferred animals to be used can be any one of the following: farm animals such as pigs and more preferably post-weaning pigs; poultry such as chickens, ducks, geese, hens or turkeys, preferably, chickens and more preferably broiler chickens; cattle such as cows, steers, bulls or oxen; game animals such as ostriches or bisons; domestic animals, for example cats or dogs; and laboratory animals, such as mice or rats. Of course, these animals are all characterized in that growth promotion and growth homogenization are desired features, in particular when meat production is the goal.

In view of the above, it will be understood that the animals may receive the strain of the invention for substantially the whole of their growing period, or for only a part of their growing period, for example the early part and/or the period leading up to slaughter.

According to a preferred aspect of the invention, the post-weaning animal is preferably a pig, preferably aged from about 10 to about 28 days old, at the onset of the trials. The pig of interest is more preferably 17 days old.

According to another preferred aspect of the invention, the post-weaning animal is preferably a mouse, preferably aged from about 18 to about 28 days old, at the onset of the trials. The mouse of interest is more preferably 21 days old.

According to yet another preferred aspect of the invention, the post-hatching animal is preferably a chicken, preferably aged from about 1 to about 7 days old, at the onset of the trials. The chicken of interest is more preferably 1 day old. It will be understood that the expression "about 1 day old" means 24 hours or less after birth or hatching.

According to a preferred aspect of the present invention, the effective amount that can be given to pigs preferably varies from $5^{E}7$ to $5^{E}9$ CFU/pig and is more preferably about $1^{E}9$ CFU/pig.

According to another preferred aspect, the effective amount that can be given to chickens varies from about $5^{E}7$ to $5^{E}9$ CFU/chicken, and is more preferably $5^{E}8$ CFU/chicken.

According to yet another preferred aspect, the effective amount that can be given to mice varies from about $5^{E}7$ to $5^{E}9$ CFU/mouse, and is more preferably $5^{E}8$ CFU/mouse.

In the particular context of the methods of the invention, the effective amount of the strain may be fed to the animal as a single dosage or may be given according to a regimen, whereby it is effective. By the term "feeding", it should be understood that an F4+ non-pathogenic *Escherichia coli* strain of the invention is provided to the animal under treatment so that the strain eventually reaches the gastrointestinal tract, and more preferably the intestines.

For instance, and according to a preferred aspect of the invention, feeding can be done by orally feeding the strain to the animal of interest.

According to a preferred aspect of the invention, the strain is preferably fed to the animal in lyophilized form. According to another preferred aspect, the strain of the invention is diluted or suspended with a diluent or carrier.

In accordance with the present invention, the F4+ non-pathogenic *Escherichia coli* strain is used to "promote growth" in an animal or to "homogenize growth among a herd animals". These expressions refer to the use of the *Escherichia coli* strain to increase an animal's growth rate. In other words, upon treatment with the strain of interest, the animal's weight increases more rapidly and more homogeneously compared with its untreated counterparts. More particularly, the expression "growth homogenization" in the context of the present invention refers to a relative control over the rate of growth in a herd of animals. This type of control bears a particular interest in the field of animal breeding and meat production in which all the animals in a given group must ideally reach their growth peak faster, at relatively the same time among the group, with conventional amounts of feed along with a non-toxic growth promoting agent. When these conditions are met, feeding costs, slaughter costs and shipping costs can all be optimized.

In order to evaluate growth promotion and growth homogenization, a number of parameters known in the field can be determined. More specifically, such parameters, evaluated either alone or in combination, can encompass:

i—Mean body weight (MBW): mean of the body weights of a group of animals;
ii—Mean daily weight gain (DWG): mean increase in weight per day, per group of animals, during a particular period;

iii—Feed intake (FI): quantity of feed ingested per animal or per group of animals during a particular period; and iv—Feed conversion ratio (FCR): feed intake per animal or per group of animals for a particular period/Weight gain for the same animal or group of animals for the same particular period.

Advantageously, the strain of the invention may be used alone or in association with a feed acceptable carrier. As used herein, the expression "feed acceptable carrier" refers to any carrier, diluent or excipient that is compatible with the strain of the invention and can be given to an animal without adverse effects. Suitable feed acceptable carriers known in the art include, but are not limited to, water, saline, glucose, dextrose, or buffered solutions. Such a carrier is advantageously non-toxic to the strain and not harmful to the animal. It may also be biodegradable. A person skilled in the art will know how to select suitable carriers, such as carriers that are not harmful to the environment. Preferably also, this carrier is a suitable solid or liquid feed acceptable carrier.

A suitable solid feed acceptable carrier is a non-toxic ingestable carrier. For instance, this solid feed acceptable carrier may be a common solid feedstuff such as the component of a typical animal diet consisting of cereal products, such as barley meal, maize meal or wheat feed, nut and seed products, such as decorticated ground nut cake or cotton seed cake, or extracted cotton seed cake, together with minor amounts of, for example, feather meal, seaweed meal, bone meal, bone flour, chalk, salt, urea and vitamins; or it may be an inert solid diluent or carrier of no nutritional value, for example kaolin, talc, calcium carbonate, fuller's earth, attapulgus clay, ground oyster shells or ground limestone; or it may be starch or lactose.

A suitable liquid feed acceptable carrier is, for example, water and preferably drinking water; milk such as whole or skim milk; or a culture medium such as a trypsone soy broth (TSB).

The following examples illustrate the wide range of potential applications of the present invention and are not intended to limit its scope. Modifications and variations can be made therein without departing from the spirit and scope of the invention. Although any method and material similar or equivalent to those described herein can be used in the practice for testing the present invention, the preferred methods and materials are described.

EXAMPLES

Example I

Description of the *Escherichia coli* strain (coliPROtec strain) and its clones

According to a preferred feature of the invention, an $F4^+$ non-pathogenic *Escherichia coli* strain (referred hereinafter as the coliPROtec or the JFF4 strain) is used. The coliPROtec strain was deposited at the International Depositary Authority of Canada on Jan. 21, 2005 and was attributed accession number IDAC 210105-01. The address for the International Depositary Authority of Canada is 1015 Arlington Street, Winnipeg, Canada, R3E 3R2.

1. Origin

The strain was isolated from feces of a healthy pig at the *Escherichia coli* Laboratory at the Faculty of veterinary medicine, University of Montreal, Saint-Hyacinthe, Quebec, Canada. Animals were purchased from a local farm located in Monteregie, Quebec, Canada.

2. Stability of the Strain

The expression of F4 fimbriae, an immunogenic protein, of the coliPROtec strain was stabilized using in vitro passages. Three (3) consecutive 10 L fermentations were done. After each fermentation, the culture was inoculated on agar and 10 colonies were tested for F4 fimbriae expression using a slide agglutination test. Bacteria from $F4^+$ colonies were pooled and used for the consecutive fermentation. The strain was then frozen in trypsone soy broth (TSB) supplemented with 20% glycerol. After thawing, the F4 expression of the strain was not totally stable and several consecutive fermentations (approximately 10) were needed to obtain a stable strain. The stable strain was freeze-dried after approximately 15 passages from the pig. This freeze-dried culture was used to produce the Master Seed of coliPROTec.

3. Biochemical Analysis

An identification of the strain was done using the API system. The identification code 5544572 obtained referred as an *Escherichia coli* strain.

4. Virotyping

Virotyping of the coliPROtec strain was done by colony hybridization and/or polymerase chain reaction (PCR). Virotyping results showed that the coliPROtec strain was positive for F4 whereas it was negative for the following toxins:

LT, STa, STb, STaH, Stx1, Stx2, VT2vp1, VT2vh, Aero, Tsh, CDT3, CDT4, CNF1, CNF2, HlyA, HlyC, Ehx, East1.

Furthermore, the coliPROtec strain was also negative for the following adhesins or putative adhesins:

F5, F6, F18, F41, F17, P fimbriae, AIDA, AFA, SFA, CS31a, daaE, Paa, aggR, ARF/1, Eae, CFAI, CFAII(CS1coo), CFAII(CS3cst).

5. DNA Fingerprinting

The coliPROtec strain was characterized using pulse-field gel electrophoresis (FIG. 1).

Particular clones of the strain, for which the F4 fimbriae expression was stable after fermentation, were selected following repeated in vitro passages.

6. Summary Table and Data Sheet

The strains used in the following experiments are described in detail in the following Table 1 and Data Sheet.

TABLE 1

| Name | Serotype | Source |
|---|---|---|
| $F4^+$ non pathogenic wild type *Escherichia coli* strains | | |
| JFF4 (coliPROtec) | O8:K87 | feces of a healthy pig |
| JG1329 | O8:K87 | feces of a pig |
| M226 | O9 | feces of a pig |
| P03-7586(175) | O8 | feces of a pig |
| $F4^+$ non pathogenic recombinant *Escherichia coli* strain | | |
| pMK005 | O9 | plasmid pMK005 coding for F4 |
| F4-negative non pathogenic *Escherichia coli* strain | | |
| P82-862 | O115:KV165 | feces of pig |

TABLE 1-continued

DATA SHEET of the coliPROtec strain

Determined with standard method of serotyping using "O" antigen and at the "Statens Serum Institut 5 Artillerivej 2300 Copenhagen S Denmark"

| | |
|---|---|
| PATHOTYPE | NEGATIVE FOR THE FOLLOWING TOXINS<br>LT, STa, STb, STaH, Stx1, Stx2, VT2vp1, VT2vh, Aero, Tsh, CDT3, CDT4, CNF1, CNF2, HlyA, HlyC, Ehx, East1<br>NEGATIVE FOR THE FOLLOWING VIRULENCE FACTORS<br>F5, F6, F18, F41, F17, P fimbriae, AIDA, AFA, SFA, CS31a, daaE, Paa, aggR, ARF/1, Eae, CFAI, CFAII(CS1coo), CFAII(CS3cst)<br>Confirmation by PCR and colony hybridization |
| MEDIUM FOR FIMBRIAE EXPRESSION | |
| ANTIBIOGRAM RESISTANT TO: | Ampicillin, tetracycline, spectinomycin, tiamulin, tylosine |
| ANTIBIOGRAM SENSITIVE TO: | Apramycin, ceftiofur, cephalothin, gentamicin, neomycin, trim/sulfamethoxazol |
| STORAGE OF MEDIUM | Freeze dried (lyophilization) medium: 5% dextran T-40, 7% saccharose, 1% monosodium glutamate |
| SOURCE OF THE ISOLATE | Isolated at The *Escherichia coli* Laboratory, Fac. méd. vét., Saint-Hyacinthe, 1999, from feces of a normal pig. |

Example II

Weaned Pigs

Effects of F4+ Non-Pathogenic *Escherichia coli* Strains, in Oral Form, on the Growth of Pigs A—Effect of coliPROtec on Weight Gain in Weaned Pigs
1. *Escherichia coli* Strain:
  The live *Escherichia coli* F4+ non-pathogenic strain coliPROtec suspended in TSB was orally fed to weaned pigs. This strain is described in Example I.
2. Experiments
2.1 Animals
  Five (5) trials were performed for a total of 45 treated and 45 untreated pigs. These pigs came from different commercial farms.
2.2 Trials
  The trials were conducted at the Faculté de médicine vétérinaire, Université de Montréal, under the following schedule.
2.2.1 Trial Groups

| GROUP NO. (n) | DESCRIPTION |
|---|---|
| 1 (45) | Untreated |
| 2 (45) | Treated with coliProtec (with $5^E9$/pig) |

2.2.2 Trial Schedule

| DAY NO. | DESCRIPTION |
|---|---|
| 1 | Arrival of the 17-day-old weaned pigs. |
| 1 To 4 | Adaptation period |
| 5 | Treatment of the animals with a single dose of coliPROtec or TSB only (control group) |
| 20 | Weighing of the animals;<br>End of the experiment. |

2.2.3 Evaluated Parameters
  In the present assays, the parameters evaluated were the weight and the daily weight gain of the weaned pigs on days 5 and 20 in Groups 1 and 2.
3. Results
  During the innocuity studies of the coliPROtec strain, a positive effect of the product was observed on the weight gain of the animals. As shown in Table 2 and 3, pigs treated with only one oral dose of coliPROtec at the beginning of the post-weaning period had a daily weight gain higher by 53 g when compared to untreated animals. Specifically, 2 weeks after the treatment, treated pigs were 849 heavier than untreated pigs.

TABLE 2

Weight of animals

| | Weight (Kg) | | | Group 2 vs |
|---|---|---|---|---|
| Day | Group 1 | Group 2 | T-test | Group 1 (g) |
| 5 | 6.053 | 6.137 | p = 0.754 | +84 |
| 20 | 12.055 | 12.904 | p = 0.020 | +849 |

TABLE 3

Daily weight gain

| | Daily weight gain (g) | | | Group 2 vs |
|---|---|---|---|---|
| Days | Group 1 | Group 2 | T-test | Group 1 (g) |
| 5 to 20 | 405 | 458 | p = 0.007 | +53 |

4. Analysis and Conclusion
  At day 5 post-weaning, giving coliPROtec, the weight of the Groups 1 and 2 (untreated and treated with coliPROtec) was not statistically different. However, at day 20 post-weaning (15 days after the treatment), the treated animals were 849 g heavier and demonstrated a daily weight gain of 53 g more than untreated animals. These differences were statistically significant.

Of note, the conventional antibiotic growth promoters generally increase the weight gain by 3.3 to 8.8% (Doyle, M. E., Food Research Institute, University of Wisconsin, 2001). As demonstrated here, the coliPROtec strain increased the daily weight gain by 11% during the 2 weeks following the single dose.

B—Effects of Live F4+ Non Pathogenic *Escherichia coli* Strains, in Oral Form, on the Growth of Weaned Pigs 1. *Escherichia coli* Strains The strains used are described in Example I.

2. Experiments 2.1. Animals

Forty nine (49) 17-day-old weaned pigs, originating from a clean, conventional pig farm, were used in the present experiments. These piglets had a body weight of 5±1 kg.

2.2. Trials 2.2.1 Trial Groups

At weaning, the pigs were transferred into the animal facilities, containment rooms, Laboratoire d'Hygiène Vétérinaire et Alimentaire, Saint-Hyacinthe, Quebec, Canada. Laboratory analyses were led at the EcL Laboratory, FMV, Saint-Hyacinthe, Quebec, Canada.

| GROUP no. (n) | DESCRIPTION |
| --- | --- |
| 1 (7) | untreated pigs |
| 2 (7) | treated with the F4-negative non pathogenic *Escherichia coli* strain P82-862 |
| 3 (7) | treated with the F4+ non pathogenic *Escherichia coli* JFF4 strain (coliPROtec) |
| 4 (7) | treated with the F4+ non pathogenic *Escherichia coli* JG1329 strain |
| 5 (7) | treated with the F4+ non pathogenic *Escherichia coli* M226 strain |
| 6 (7) | treated with the F4+ non pathogenic *Escherichia coli* P03-7586(175) strain |
| 7 (7) | treated with the F4+ non pathogenic recombinant *Escherichia coli* pMK005 strain. |

2.2.2 Trial Schedule

| DAY no. | DESCRIPTION |
| --- | --- |
| 0 | Arrival of the 17-day-old weaned pigs at the animal facilities. |
| 1 | Identification, grouping and weighing of pigs. Grouping according to animal sex and weight. Sampling of feces for evaluation of the excretion of F4, LT, STa and/or STb positive *Escherichia coli* (PCR) |
| 1 and 4 | Approximately 5E9 CFU of *Escherichia coli* bacteria in trypsone soy broth (TSB) per pig given orally using an oesophageal tube. The control group received TSB only. |
| 1, 4, 9, 14 and 17 | Weighing of the animals; sampling of feces for evaluation of the excretion of F4, LT, STa and/or STb positive *Escherichia coli* (PCR) |
| 17 | Euthanasia of animals |

2.2.3 Evaluated Parameters

During the trial, pigs had ad libitum access to feed and water. They were observed twice daily for general health and presence of diarrhea. From day 0 to day 14, pigs were fed with a commercial starter feed containing 23% protein without addition of zinc oxide or antibiotics. For the last 3 days, the feed contained 19% protein.

3. Results 3.1 F4+ *Escherichia coli* and Pathogenic ETEC Status of Pigs

At the beginning of the trial, thus before treatment, some pigs from all groups were colonized by an F4+ strain possessing the toxin STb (Table 4). All pigs of the control group (Group 1) and of the group treated with an F4− *Escherichia coli* strain (Group 2), were colonized by this F4:STb strain at day 9 (Table 5). Although this strain (O45:F4:STb) is not a usual ETEC strain causing post-weaning diarrhea in pigs, we can not exclude that it is pathogenic. However, no animal demonstrated clinical signs associated with post-weaning diarrhea during the trial.

Since both control groups were colonized by this F4+ strain, it is difficult to evaluate the effect of the tested F4+ strains on animal growth performance.

TABLE 4

Identification of the status of pigs for excretion of F4+ *Escherichia coli* strain before treatment (Day 1; PCR analysis on feces)

| | Number of pigs with feces positive for F4 | Other virulence factors identified |
| --- | --- | --- |
| Group 1*1 | 1 | LT and STb |
| Group 2 | 1 | STb |
| Group 3 | 2 | LT and STb |
| Group 4 | 1 | LT and STb |
| Group 5 | 1 | LT and STb |
| Group 6 | 3 | LT and STb |
| Group 7 | 1 | STb |

*1Treatment: Group 1; control, Group 2; F4-negative *Escherichia Coli* strain at days 1 and 4, Groups 3 to 7; F4+ strains at days 1 and 4.

TABLE 5

Identification of the status of pigs for excretion of F4+ *Escherichia coli* strains during the trial

| | Number of pigs with feces positive for F4 | | | | |
| --- | --- | --- | --- | --- | --- |
| | Day 1*1 | Day 4 | Day 9 | Day 14 | Day 17 |
| Group 1*1 | 1 | 3 | 7 | 4 | 0 |
| Group 2 | 1 | 2 | 7 | 3 | 0 |
| Group 3 | 2 | 4 | 6 | 5 | 5 |
| Group 4 | 1 | 7 | 7 | 6 | 0 |
| Group 5 | 1 | 6 | 6 | 5 | 6 |
| Group 6 | 3 | 1 | 1 | 7 | 4 |
| Group 7 | 1 | 1 | 1 | 0 | 0 |

*1Treatment: Group 1; control, Group 2; F4-negative *Escherichia coli* strain at days 1 and 4, Groups 3 to 7; F4-positive strains at days 1 and 4.

3.2 General Health and Diarrhea Assessment

All animals were in good health during the trial. Some animals of groups 2, 3, 4, 6 and 7 presented mild diarrhea, but for only one day.

3.3 Growth Performance Assessment

TABLE 6

Weight of pigs after treatment with F4+ *Escherichia coli* strains

| | Body weight (Kg) | | | | |
| --- | --- | --- | --- | --- | --- |
| | Day 1*1 | Day 4 | Day 9 | Day 14 | Day 17 |
| Group 1*1 | 4.91 | 5.43 | 6.74 | 9.09 | 10.23 |
| Group 2 | 4.86 | 5.40 | 7.11 | 9.23 | 11.20 |
| Group 3 | 4.91 | 5.77 | 7.23 | 9.34 | 10.91 |
| Group 4 | 5.00 | 5.13 | 7.07 | 9.20 | 10.60 |
| Group 5 | 4.97 | 5.59 | 7.04 | 9.27 | 10.47 |
| Group 6 | 4.91 | 5.47 | 7.20 | 9.41 | 10.46 |
| Group 7 | 5.03 | 5.80 | 8.03 | 10.20 | 11.23 |

*1Treatment: Group 1; control, Group 2; F4-negative *Escherichia coli* strain at days 1 and 4, Groups 3 to 7; F4-positive strains at days 1 and 4.

The linear model with repeated measures, using the day as within-subject factor and the group as between-subject factor, showed no effect of treatment on growth of pigs (p=0.90). Post hoc analysis checked for differences between each treated group (groups 2 to 7) and the control group (group 1) at each day (Table 6). Weight was significantly higher for group 7, compared to the control group, at day 9 only (p=0.045). Other weight differences were not significant.

Figure 2:
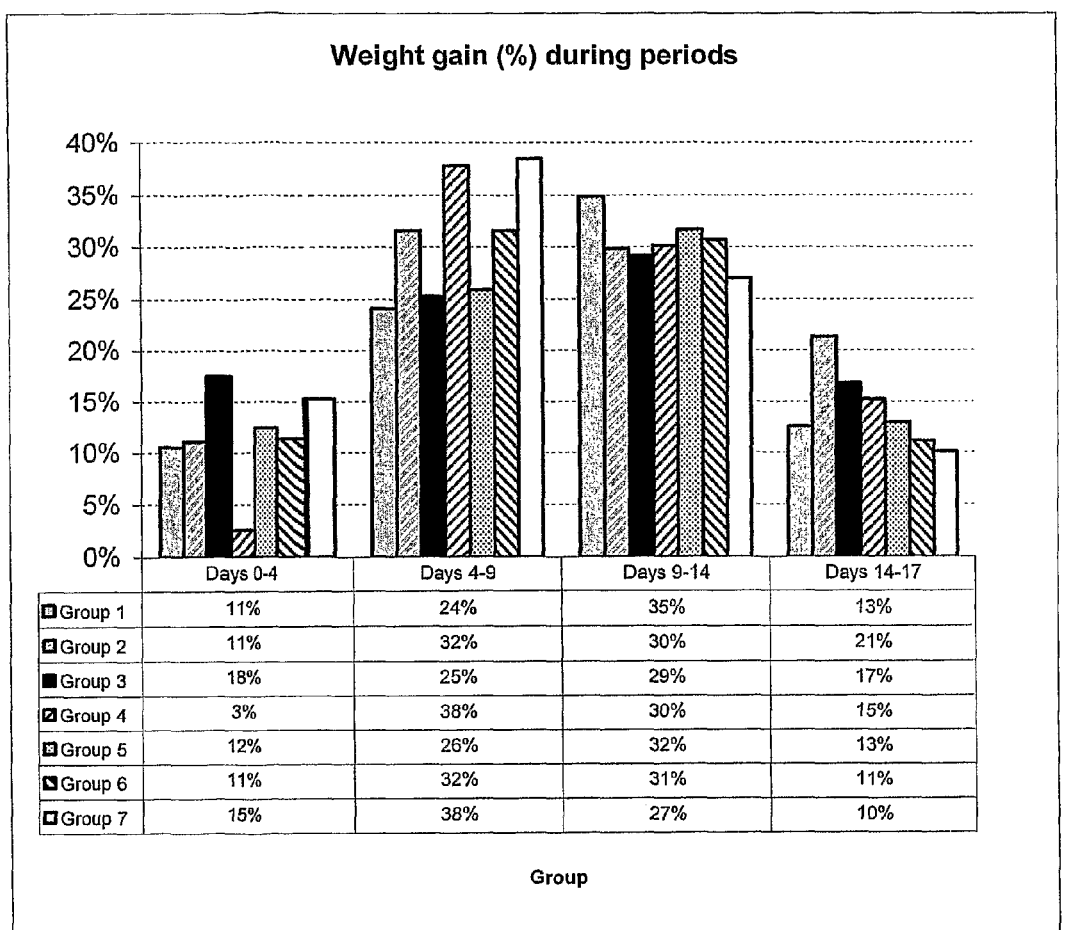
FIG. 2 is a graph that displays the percentage of weight gain in pigs for each period after treatment with $F4^+$ *Escherichia coli* strains.

Nevertheless, Groups 3 and 7, treated with the JFF4 and the recombinant strains, respectively, had a higher weight at days 4 and 9, but weights were subsequently more similar between groups (Table 6). During the first period of the trial (days 0 to 4), groups 3 and 7 had a percentage of weight gain of 18 and 15%, respectively, compared to 11% for both control groups (Groups 1 and 2; FIG. 2). The low weight gain observed for the group 4 during this first period was attributed to 3 pigs that lost weight.

During the second period (days 4 to 9), groups 2, 4, 6 and 7 had a higher percentage of weight gain than that of the untreated group (group 1). The percentage of weight gain was more homogeneous during the third period (days 9 to 14) and was higher for groups 2 and 3 than for group 1, during the last period.

Example III

Broiler Chickens

Effects of Live F4$^+$ Non Pathogenic *Escherichia coli* Strains, in Oral Form, on the Growth of Broiler Chickens 1. *Escherichia coli* Strains
The strains used are described in Example I.
2. Experiments
2.1 Animals
Sixty-three (63) male 1-day-old Cobbs broiler chicks, originating from a clean, conventional chicken farm. After hatching, chicks were transferred into animal facilities.
2.2 Trials
2.2.1 Trial Groups
At hatching, the chickens were transferred into the animal facilities, containment rooms, Faculté de médecine vétérinaire, Saint-Hyacinthe, Quebec, Canada.
Laboratory analyses were led at the EcL Laboratory, FMV, Saint-Hyacinthe, Quebec, Canada.

| GROUP NO. (N) | DESCRIPTION |
|---|---|
| 1 (10) | untreated chickens |
| 2 (10) | treated with the F4-negative non pathogenic *Escherichia coli* strain P82-862 |
| 3 (10) | treated with F4$^+$ non pathogenic *Escherichia coli* JFF4 strain (coliPROtec) |
| 4 (10) | treated with the F4$^+$ non pathogenic *Escherichia coli* JG1329 strain |
| 5 (10) | treated with the F4$^+$ non pathogenic *Escherichia coli* M226 strain |
| 6 (10) | treated with the F4$^+$ non pathogenic *Escherichia coli* P03-7586(175) strain |
| 7 (10) | treated with the F4$^+$ non pathogenic recombinant *Escherichia coli* pMK005 strain. |

2.2.2 Trial Schedule

| DAY NO. | DESCRIPTION |
|---|---|
| 0 | Arrival of the 1 day-old chicks at the animal facilities; identification, Weighing and grouping of chicks; Sampling of feces for evaluation of the excretion of F4, LT, STa and/or STb positive *Escherichia coli* (PCR) |
| 1 and 4 | Approximately 1E9 CFU of *Escherichia coli* bacteria in trypsone broth (TSB) per chick given orally using an oesophageal needle. The control group received TSB only |
| 0, 4, 9, 14, 18, 23 and 28 | Weighing of the animals; evaluation of the excretion of F4, LT, STa and/or STb positive *Escherichia coli* (PCR) |
| 2, 9, 17 and 24 | Evaluation of the 24 hour feed consumption |
| 28 | Euthanasia of animals |

2.2.3 Evaluated Parameters
Mean body weight (MBW), Mean daily weight gain (DWG), feed intake (FI), and feed conversion ratio (FCR) were all evaluated in the present assays.

During the trial, chickens had ad libitum access to feed and water. They were observed twice daily for the general health and presence of diarrhea. From day 0 to day 24, chickens received a standard commercial feed for chicks (without antibiotics). From day 24 to day 28, they received a standard development commercial feed (without antibiotics).

3. Results
3.1 F4$^+$ *Escherichia coli* and Pathogenic ETEC Status of Chickens

No fecal sample was positive for F4, STa, STb or LT at day 0, before treatment. Fecal excretion of F4$^+$ *Escherichia coli* was detected in treated groups (groups 3 to 7) at days 2 and 4, but not subsequently.

3.2 General Health and Diarrhea Assessment

Animals were in good health during the trial and no diarrhea was observed. Three (3) animals of group 7 were euthanized at day 23 or 25 due to their deteriorating general health status. No gastro-intestinal clinical sign was observed in these chickens. Necropsy reports on these chickens from the Pathology department (Faculté de médecine vétérinaire, Saint-Hyacinthe, Quebec, Canada) revealed that these chickens died from the ascites syndrome, a frequent non infectious disease, generally associated with cardiac insufficiency, in broiler chickens.

3.3 Growth Performance Assessment

TABLE 7

Weight of chickens after treatment with F4$^+$ *Escherichia coli* strains

| Group | Mean body weight (g) | | | | | | |
|---|---|---|---|---|---|---|---|
|  | 0 | 4 | 9 | 14 | 18 | 23 | 28 |
| 1[*1] | 42, 11 | 93, 22 | 170, 89 | 411, 00 | 655, 56 | 1018, 67 | 1386, 22 |
| 2 | 43, 89 | 94, 33 | 174, 56 | 395, 11 | 644, 44 | 968, 56 | 1341, 11 |
| 3 | 42, 11 | 89, 67 | *illegible* | *illegible* | *illegible* | 1003, 22 | 1305, 89 |
| 4 | 40, 89 | 88, 00 | *illegible* | 405, 56 | 645, 78 | 1019, 44 | 1326, 56 |
| 5 | 40, 44 | 96, 78 | *illegible* | *illegible* | *illegible* | *illegible* | 1322, 67 |
| 6 | 39, 56 | 91, 33 | *illegible* | *illegible* | *illegible* | *illegible* | 1372, 33 |
| 7 | 40, 78 | 95, 67 | *illegible* | *illegible* | *illegible* | *illegible* | 1492, 83[*2] |

[*1] Treatment: Group 1; control, Group 2; F4-negative *Escherichia coli* strain at days 1 and 4, Groups 3 to 7; F4-positive strains at days 1 and 4.
[*2] Three euthanized animals were excluded

TABLE 8

Daily weight gain of chickens after treatment with F4+ Escherichia coli strains

| Group | Mean daily weight gain (g) | | | | | |
|---|---|---|---|---|---|---|
| | 0-4 | 4-9 | 9-14 | 14-18 | 18-23 | 23-28 |
| 1[*1] | 12,8 | 15,5 | 48,0 | 61,1 | 75,6 | 73,5 |
| 2 | 12,6 | 16,0 | 44,1 | 62,3 | 64,8 | 74,5 |
| 3 | 11,9 | [illegible] | 48,0 | [illegible] | 63,5 | 60,5 |
| 4 | 11,8 | [illegible] | 45,5 | 60,1 | 74,7 | 61,4 |
| 5 | 14,1 | [illegible] | 48,4 | [illegible] | 68,2 | 57,2 |
| 6 | 12,9 | [illegible] | 48,4 | 62,2 | 72,9 | 65,8 |
| 7 | 13,7 | [illegible] | [illegible] | 58,4 | 73,4 | 76,7[*2] |

[*1]Treatment: Group 1; control, Group 2; F4-negative *Escherichia coli* strain at days 1 and 4, Groups 3 to 7; F4-positive strains at days 1 and 4.
[*2]Three euthanized animals were excluded Strain JFF4: The MBW of group 3, treated with the strain JFF4, was higher than for the untreated group (group 1) and the group treated with the F4-negative strain (group 2) on days 9, 14, 18 (Table 7). The DWG of the group treated with strain JFF4 was higher than for both control groups (groups 1 and 2) during the days following the second treatment (period between days 4 and 9) and during the fourth period (days 14 to 18; Table 8).

Other F4[30] strains: The MBW of groups 5, 6, and 7 was higher than that of both control groups (groups 1 and 2) on days 6, 14, 18, and 23. By contrast, it was higher only on day 9 for group 4 (Table 7).

The DWG of all groups treated with F4+ strains was higher than that of both control groups during the days following the treatments (days 4 to 9) and during the fourth period (days 14 to 18) for group 5 (Table 8).

F4-negative Strain:

The MBW and DWG were similar or lower for the group treated with the F4-negative strain than for the untreated group.

A linear model with repeated measures, using the day as within-subject factor and the group as between-subject factor, showed no effect of treatment on growth of chickens (p=0.97). Post hoc analysis was done to check for differences between each treated group (groups 2 to 7) and the untreated group (group 1) on each day. Weight was not significantly different between each treated group and the untreated group on each day. Differences observed in the descriptive analysis were not significant probably due to a higher variability than expected for the weight of chickens in each group, in particular for the untreated group.

3.4 Feed Intake (FI)

TABLE 9

Feed intake (24-hr-period) of chickens after treatment with F4+ Escherichia coli strains

| Group | Feed intake (g) of groups (per animals) for 24-hour-periods | | | |
|---|---|---|---|---|
| | Day 2 | Day 9 | Day 17 | Day 24 |
| 1[*1] | 144 (16, 0) | 576 (64, 0) | 1043 (115, 9) | 1316 (146, 2) |
| 2 | 146 (16, 2) | 522 (58, 0) | 951 (1057, 7) | 1180 (131, 1) |
| 3 | [illegible] | 570 (63, 3) | [illegible] | 1305 (145, 0) |
| 4 | [illegible] | [illegible] | [illegible] | 1389 (154, 3) |
| 5 | 169 (18, 8) | 526 (58, 4) | 976 (108, 4) | 1274 (141, 6) |
| 6 | 145 (16, 1) | 632 (70, 2) | [illegible] | 1535 (170, 6) |
| 7 | 144 (16, 0) | 695 (77, 2) | 1013 (112, 6) | 1006[*2] (143, 7) |

[*1]Treatment: Group 1; control, Group 2; F4-negative *Escherichia coil* strain at days 1 and 4, Groups 3 to 7; F4-positive strains at days 1 and 4.
[*2]Two euthanized animals (n = 7 instead of 9)

Strain JFF4: The FI of group 3 (JFF4) was lower than that of both the untreated group (group 1) and the group treated with the F4-negative strain (group 2) at days 2, and 17 (Table 9).

Other F4+ strains: The FI was lower than that of both control groups (groups 1 and 2) only for group 4 (days 2, 9, 17) and for group 6 (day 17).

F4-negative strain: The FI of the group treated with an F4-negative strain was lower than that of the untreated group (group 1) at days 9, 17, and 24.

A linear model showed no effect of treatment on feed consumption of chickens (p=0.77).

3.5 Feed Conversion Ratio (FCR)

TABLE 10

Feed conversion ratio of chickens after treatment with F4+ Escherichia coli strains

| Group | Feed conversion ratio[*1] of groups | | | |
|---|---|---|---|---|
| | Day 2 | Day 9 | Day 17 | Day 24 |
| 1[*2] | 1,25 | 2,01 | 1,90 | 2,01 |
| 2 | 1,29 | 1,93 | 1,70 | 2,02 |
| 3 | [illegible] | 1,91 | [illegible] | 2,28 |
| 4 | 1,28 | [illegible] | [illegible] | 2,07 |
| 5 | 1,33 | [illegible] | [illegible] | 2,08 |
| 6 | 1,24 | 2,07 | [illegible] | 2,34 |
| 7 | [illegible] | 2,27 | 1,93 | 1,96[*3] |

[*1]Day 2; total DWG of the group between days 0 and 4/FI at day 2, Day 9; total DWG of the group between days 4 and 14/FI at day 9, Day 17; total DWG of the group between days 14 and 23/FI at day 17, Day 24; total DWG of the group between days18 and 28/FI at day 24.
[*2]Treatment: Group 1; control, Group 2; F4-negative *Escherichia coil* strain at days 1 and 4, Groups 3 to 7; F4-positive strains at days 1 and 4.
[*3]Two euthanized animals (n = instead of 9)

Strain JFF4: The FCR of group 3 (JFF4), was lower than that of both the untreated group (group 1) and the group treated with the F4-negative strain (group 2) at days 2, and 17 (Table 10), similarly to the FI (Table 9). This ratio was lower than that of the untreated group, only at day 9.

Other F4+ strains: The FCR was lower than that of both control groups (groups 1 and 2) for group 7 (day 2), groups 3 and 4 (days 9 and 17), and groups 3 and 6 (day 17; table 4)

F4-negative strain: The FCR of the group treated with an F4-negative strain was lower than that of the untreated group (group 1), at day 17 only.

A linear model showed no effect of treatment on the feed conversion ratio of chickens (p=0.68).

4. Analysis and Conclusion

Results demonstrate that F4$^+$ non-pathogenic *E. coli* strains, including the JFF4 strain, increase the growth performance of chickens. The growth performance was positively affected, especially for the days immediately following the second treatment, the DWG being higher for all treated groups than for the untreated group, during days 4 to 9. Two F4$^+$ strains, including the JFF4 strain, also had a higher DWG than both control groups during days 14 to 18. The improvement in the growth performance during the days immediately following treatments (days 4 to 9) resulted in a higher weight for groups treated with F4$^+$ strains than for both control groups until day 18 or, for some groups, day 23.

The higher DWG observed during the short period post-treatment affected positively the MBW of treated groups until days 18 or 23, depending on the strain. Greater weight of treated groups was not associated with higher feed intake. Furthermore, FI was sometimes lower for the treated groups than for the untreated group, thus lowering the feed conversion ratio.

This effect on growth performance is associated with the F4 determinant or with strains expressing the F4 determinant since the group treated with the F4-negative *Escherichia coli* strain did not show this effect and had similar growth performance to the untreated group.

Example IV

Weaned Mice

Effects of Live F4$^+$ Non Pathogenic *Escherichia coli* Strains, in Oral Form, on the Growth of Weaned Mice 1. *Escherichia coli* Strains The strains used are described in Example I.

2. Experiments 2.1 Animals

Seventy (70) healthy 21-day-old weaned mice. At weaning, mice were transferred into the animal facilities.

2.2 Trials 2.2.1 Trial Groups

At weaning, the mice were transferred into the animal facilities, containment rooms, Laboratoire d'Hygiène Vétérinaire et Alimentaire, Saint-Hyacinthe, Quebec, Canada. The trials were also led at the EcL Laboratory, FMV, Saint-Hyacinthe, Quebec, Canada.

| GROUP NO. (N) | DESCRIPTION |
|---|---|
| 1 (10) | untreated mice |
| 2 (10) | treated with the F4-negative non pathogenic *Escherichia coli* strain P82-862 |
| 3 (10) | treated with the F4$^+$ non pathogenic *Escherichia coli* JFF4 strain (coliPROtec) |
| 4 (10) | treated with the F4$^+$ non pathogenic *Escherichia coli* JG1329 strain |
| 5 (10) | treated with the F4$^+$ non pathogenic *Escherichia coli* M226 strain |
| 6 (10) | treated with the F4$^+$ non pathogenic *Escherichia coli* P03-7586(175) strain |
| 7 (10) | treated with the F4$^+$ non pathogenic recombinant *Escherichia coli* pMK005 strain. |

2.2.2 Trial Schedule

| DAY NO. | DESCRIPTION |
|---|---|
| 0 | Arrival of the 21 day-old weaned mice at the animal facilities; identification, weighing and grouping of mice; for each treated group, 5 males and 5 females were grouped in 2 cages. Sampling of feces for evaluation of the excretion of F4, LT, STa and/or STb positive *Escherichia coli* (PCR) |
| 1 and 4 | Approximately 1E9 CFU of *Escherichia coli* bacteria in trypsone broth (TSB) per mice given orally using an oesophangeal needle. The control group received TSB only. |
| 1, 4, 9, 14, 18, 23 and 28 | Weighing of the animals; evaluation of the feed consumption for the period from the day of the previous weighing to the day of the weighing. Feces were sampled for evaluation of excretion of F4, LT, STa and/or STb positive *Escherichia coli* (PCR) |
| 28 | Euthanasia of animals |

Variables evaluated: Mean body weight gain (MBW), feed intake (FI), and feed conversion ratio (FCR).

During the trial, mice had ad libitum access to feed and water. They were observed twice daily for general health and presence of diarrhea.

3. Results 3.1. F4$^+$ *Escherichia coli* and Pathogenic ETEC Status of Mice

No fecal sample was positive for F4, STa, STb or LT at day 0. F4 was identified in the feces of groups 3, 4, 5 and 7 on the day after the first and/or up to 10 days after the second treatment with the F4$^+$ strains. No STa, STb or LT was detected at any time during the experiment.

3.2. General Health and Diarrhea Assessment

All animals were in good health during the trial and no diarrhea was observed.

3.3. Growth Performance Assessment

TABLE 11

Mean body weight of mice after treatment with F4$^+$ *Escherichia coli* strains

| | Body weight (g) | | | | | | |
|---|---|---|---|---|---|---|---|
| Group | Day 0 | Day 4 | Day 9 | Day 14 | Day 18 | Day 23 | Day 28 |
| 1*[1] | 16.71 | 21.01 | 23.67 | 24.95 | 26.15 | 27.35 | 28.24 |
| 2 | 17.20 | 21.67 | 24.40 | 25.72 | 26.81 | 28.32 | 29.38 |
| 3 | 17.33 | 21.93 | 24.42 | 25.85 | 27.10 | 27.88 | 28.94 |
| 4 | 17.54 | 21.39 | 24.37 | 26.12 | 26.87 | 28.09 | 29.48 |
| 5 | 18.05 | 21.68 | 24.40 | 25.70 | 27.42 | 28.85 | 29.90 |
| 6 | 17.77 | 21.52 | 24.37 | 25.83 | 26.92 | 27.89 | 29.13 |
| 7 | 17.79 | 20.88 | 23.44 | 24.03 | 26.15 | 27.41 | 28.29 |

*[1]Treatment: Group 1; control.Group 2; F4-negative *Escherichia coli* strain at days 1 and 4, Groups 3 to 7; F4-positive strains at days 1 and 4.

No difference in body weight was observed between groups. Linear model with repeated measures, using the day as within-subject factor and the group as between-subject factor, showed no effect of treatment on growth of mice (p=0.99). Post hoc analysis checked for differences between each treated group (groups 2 to 7) and the control group (group 1) on each day. Weight was not different between each treated group and the control group on each day.

Figure 3:
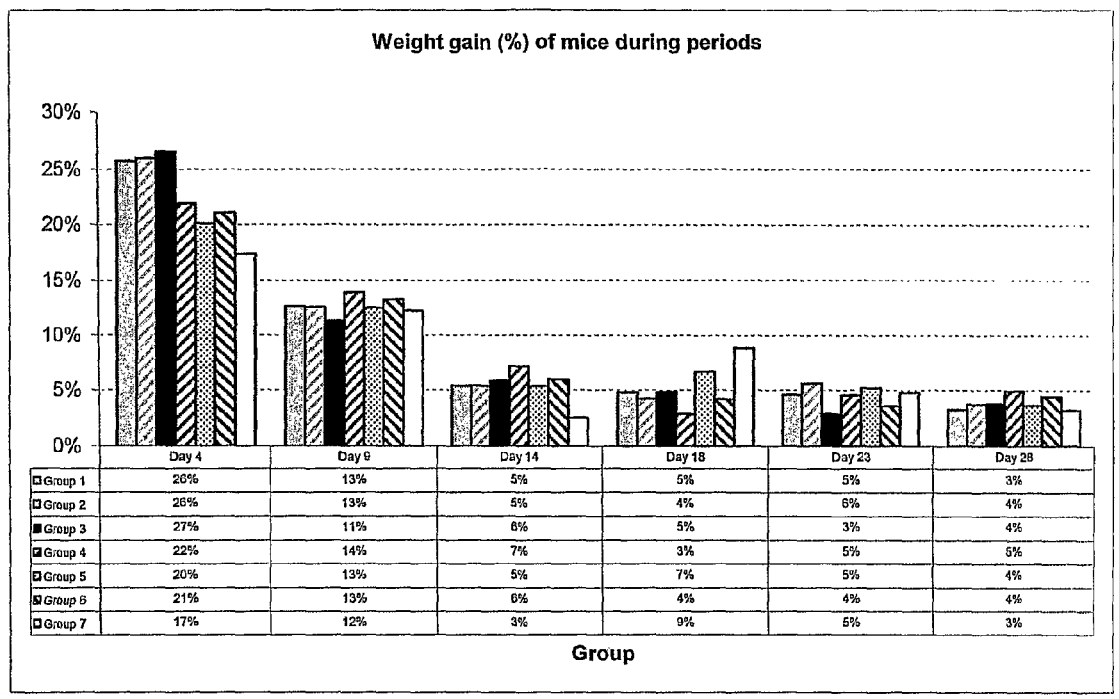
FIG. 3 is a graph that displays the percentage of weight gain in mice after treatment with $F4^+$ *Escherichia coli* strains.

Percentages of weight gain of all groups were similar during the trial period of 28 days. On the other hand, groups 1, 2, and 3 had slightly greater increase, at day 4 only (FIG. 3).

3.4 Feed Intake (FI)

TABLE 12

Feed intake of mice after treatment with F4+ *Escherichia coli* strains

| Group | Feed intake (g) of groups for each trial period | | | | | |
|---|---|---|---|---|---|---|
| | 0 to 4 | 4 to 9 | 9 to 14 | 14 to 18 | 18 to 23 | 23 to 28 |
| 1*1 | 148, 1 | 198, 1 | 243, 2 | 176, 2 | 209, 2 | 208, 6 |
| 2 | 149, 4 | 192, 6 | 201, 6 | 165, 4 | 192, 2 | 191, 6 |
| 3 | 154, 1 | [illegible] | 208, 6 | 176, 1 | 195, 6 | 195, 1 |
| 4 | [illegible] | [illegible] | [illegible] | [illegible] | [illegible] | [illegible] |
| 5 | 157, 4 | [illegible] | 224, 8 | 182, 0 | 207, 8 | 205, 5 |
| 6 | 161, 6 | [illegible] | 219, 4 | 180, 0 | 187, 6 | 215, 0 |
| 7 | 153, 0 | [illegible] | 198, 8 | 179, 4 | 190, 0 | 190, 9 |

*1Treatment: Group 1; control, Group 2; F4-negative *Escherichia coli* strain on days 1 and 4, Groups 3 to 7; F4+ strains on days 1 and 4.

Strain JFF4: The FI of group 3 (JFF4), was lower than that of both the untreated group (group 1) and the group treated with the F4-negative strain (group 2) between days 4 to 9, early after treatment. However, it was lower than that of the untreated group but similar to that of the group treated with the F4-negative strain for most of the following periods, except days 14 to 18 (Table 12).

Other F4+ strains: The FI of all other F4+ strains was lower than that of both control groups (groups 1 and 2) during the period days 4 to 9, early after the treatment (Table 12). Subsequently, the FI varied, depending on the strain (Table 12).

F4-negative strain: The FI of the group treated with an F4-negative strain (group 2) was similar to that observed for the untreated group (group 1) until day 9, and was subsequently lower than the latter. Thus, the reduction of the FI for group 2 was observed later after treatment than for groups treated with F4+ strains.

The linear model showed a significant effect of the treatment on feed intake (p<0.0001). Post-hoc Dunnett's test showed that the feed consumption was significantly higher for the control group (Group 1) than for the groups 2, 3, 4, and 7, treated with the 862, JFF4, JG1329, and pmK005 strains, respectively (Table 12). For these groups, mice ate less feed to reach the same weight.

3.5 Feed Conversion Ratio (FCR)

TABLE 13

Feed intake of mice after treatment with F4+ *Escherichia coil* strains

| Group | Feed conversion ratio of groups | |
|---|---|---|
| | Days 0-14 | Days 14-28 |
| 1*1 | 7, 30 | 18, 39 |
| 2 | 6, 50 | 14, 96 |
| 3 | [illegible] | 18, 34 |
| 4 | 6, 62 | 17, 11 |
| 5 | 7, 40 | 14, 17 |
| 6 | 7, 04 | 17, 65 |
| 7 | 8, 44 | 13, 15 |

*1Treatment: Group 1; control, Group 2; F4-negative *Escherichia coli* strain at days 1 and 4, Groups 3 to 7; F4+ strains at days 1 and 4.

Although the difference was not significant, the FCR of the group treated with JFF4 was lower than that of any other treatment group for days 0 to 14. Subsequently, the FCR was more variable between groups. The linear model showed no significant effect of the treatment on the FCR.

4. Analysis and Conclusion

The effect of F4+ *Escherichia coli* strains on growth seems to be less important than that observed for pigs and chickens. Nevertheless, an effect on the FI and the FCR was observed, particularly during the growth phase of the mice (first 14 days). Since CD-1 mice were not genetically selected for growth performance, as was the case for the chickens and pigs used in the present studies, it is possible that the mice rapidly reached the maximum weight gain and that there was thus little scope for the F4+ strains to influence weight gain, thus affecting only feed intake.

Bernardeau et al. reported that the growth promoting effect of *Lactobacilli* was not observed in mice overfed with conventional enriched diets whereas the impact of probiotic administration was enhanced in mice fed a sub-standard diet (such as one based on barley).

REFERENCES

Arnold S., Gassner B., Giger T. and Zwahlen R. Banning antimicrobial growth promoters in feedstuffs does not result in increased therapeutic use of antibiotics in medicated feed in pig farming. *Pharmacoepidemiology and Drug Safety* 2004; 13: 323-331.

Wegener H C, Aarestrup F M, Bogo Jensen L, Hammerum A M and Bager F. Use of antimicrobial growth promoters in food animals and Enterococcus faecium resistance to therapeutic antimicrobial drugs in Europe. *Emerging Infectious Diseases* 1999; 5 (3): 329- 335.

Schwarz S, Kehrenberg C and Walsh T R. Use of antimicrobial agents in veterinary medicine and food animal production. *International Journal of Antimicrobial Agents* 2001; 17: 431-437.

Bernardeau M, Vernoux J P and Gueguen M. Safety and efficacy of probiotic lactobacilli in promoting growth in post-weaning Swiss mice. *International Journal of Food Microbiology* 2002; 77(1-2): 19-27.

What is claimed is:

1. Method of promoting growth of an animal, comprising the step of:
   feeding the animal with an F4+ non-pathogenic *Escherichia coli* strain, wherein the F4+ non-pathogenic *Escherichia coli* strain is in an amount effective to promote growth of the animal.

2. The method according to claim 1, wherein the step of feeding comprises feeding orally.

3. The method according to claim 2, wherein said F4+ non-pathogenic *Escherichia coli* strain is in association with an acceptable carrier selected from the group consisting of a solid feed acceptable carrier, a liquid feed acceptable carrier, and a combination thereof.

4. The method according to claim 3, wherein the solid feed acceptable carrier comprises a common solid feedstuff.

5. The method according to claim 3, wherein the liquid feed acceptable carrier comprises water.

6. The method according to claim 3, wherein the liquid feed acceptable carrier comprises milk.

7. The method according to claim 1, wherein the effective amount is at least about $5\times10^7$ CFU of F4+ non-pathogenic *Escherichia coli* strain per animal.

8. The method according to claim 1, wherein the effective amount ranges from about $5\times10^7$ to about $5\times10^9$ CFU of F4+ non-pathogenic *Escherichia coli* strain per animal.

9. The method according to claim 1, wherein the F4+ non-pathogenic *Escherichia coli* strain consists of the *Escherichia coli* strain deposited at the International Depository Authority of Canada IDAC on Jan. 21, 2005 under accession number IDAC 210105-01, mutants or variants thereof.

10. The method according to claim 1, wherein the animal is selected from the group consisting of a post-weaning animal, a post-hatching animal, and a combination thereof.

11. The method according to claim 10, wherein the animal is a post-weaning animal aged from about 10 to about 28 days old.

12. The method according to claim 10, wherein the animal is a post-hatching animal aged from about 1 to about 7 days old.

13. The method according to claim 10, wherein the animal is a post-weaning pig.

14. The method according to claim 10, wherein the animal is a post-weaning mouse.

15. The method according to claim 10, wherein the animal is a post-hatching poultry animal.

16. The method according to claim 15, wherein the poultry animal is a chicken.

17. The method according to claim 1, wherein said F4+ non-pathogenic *Escherichia coli* strain promotes daily weight gain.

18. The method according to claim 1, wherein said F4+ non-pathogenic *Escherichia coli* strain promotes weight gain while reducing feed intake.

19. The method according to claim 1, wherein said F4+ non-pathogenic *Escherichia coli* strain is fed to the animal during the animal's growth phase and reduces the delay required for the animal to attain a desired weight.

* * * * *